United States Patent [19]

Sacks et al.

[11] Patent Number: 4,826,481

[45] Date of Patent: May 2, 1989

[54] ENTERAL FEEDING DEVICE

[75] Inventors: Barry A. Sacks, Newton; Arnold S. Gould, Bedford; Michael P. Manzo, Southboro; Michael A. Ciannella, Marlboro, all of Mass.

[73] Assignee: Abbott Labs., Abbott Park, Ill.

[21] Appl. No.: 178,835

[22] Filed: Mar. 24, 1988

Related U.S. Application Data

[63] Continuation of Ser. No. 54,572, May 27, 1987, abandoned.

[51] Int. Cl.$^4$ ............................................. A61M 25/00
[52] U.S. Cl. ................................... 604/54; 604/104; 604/164
[58] Field of Search ............................ 604/104–107, 604/264, 164, 174, 175, 280, 282

[56] References Cited

U.S. PATENT DOCUMENTS

| | | | |
|---|---|---|---|
| 2,340,068 | 1/1944 | Limpert | 604/104 |
| 2,649,092 | 8/1953 | Wallace | 604/105 |
| 3,490,457 | 1/1970 | Peterson | 604/105 |
| 3,592,197 | 7/1971 | Cohen | 604/106 |
| 3,640,281 | 2/1972 | Robertson | 604/264 |
| 4,069,826 | 1/1978 | Sessions et al. | 604/105 |
| 4,072,249 | 2/1978 | Ekenstam et al. | 604/212 |
| 4,389,210 | 6/1983 | Genese | 604/177 |

OTHER PUBLICATIONS

Gauderer and Ponsky, "A Simplified Technique For Constructing a Feed Tube Gastrostomy", *Surgery, Gynecology & Obstetrics*, vol. 152, 82–85 Jan. 1981.

Cordis, 1972 *Cordis Ducor Accessories to the Angiographic System.*

Primary Examiner—Stephen C. Pellegrino
Attorney, Agent, or Firm—Donald O. Nickey; Edward H. Gorman, Jr.

[57] ABSTRACT

An enteral feeding catheter is characterized by being adapted for introduction through the mouth via a guidewire that extends from the mouth through the esophagus, stomach and abdominal puncture. The catheter has a relatively stiff leading portion of length sufficient to extend along the guidewire from the mouth through the abdominal puncture and of stiffness sufficient to permit it to be pushed along the guidewire, at least an initial length of the catheter being tapered to a narrow leading tip to enable the puncture to be dilated as its drawn therethrough. The catheter also has a relatively soft, large diameter trailing portion connected to the leading portion adapted to be drawn along said guidewire by grasping and pulling the stiff leading portion until the leading end of the soft portion extends outside the body through the widened puncture, while the trailing end remains in the stomach, whereby the relatively soft trailing portion can serve as a conduit for enteric feeding. A method of placing the device for enteral feeding is described, as is a retractable locking device of special configuration for use with the soft portion of this catheter, or others, the lock providing a relatively large, compared to the opening in an associated retainer, fixed protuberance about the catheter to prevent passage of the catheter through the opening absent application of abnormally high pulling force.

29 Claims, 4 Drawing Sheets

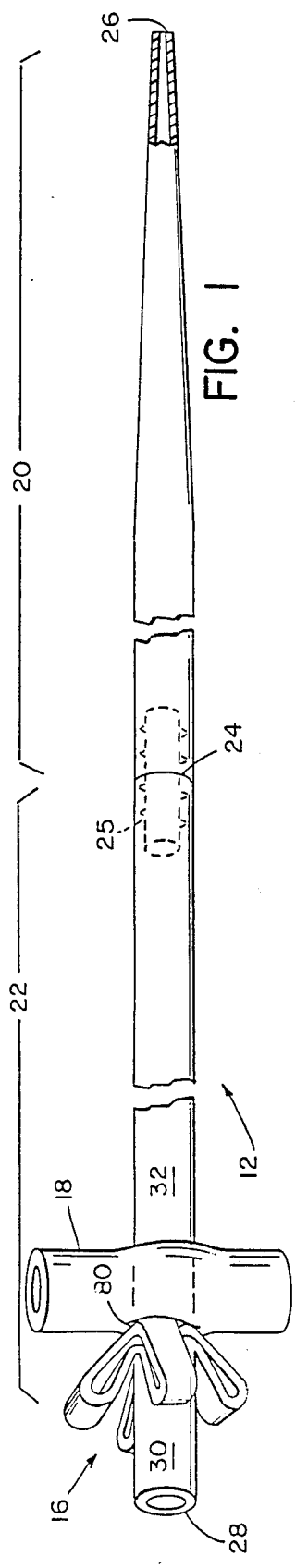
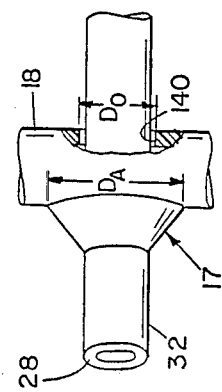
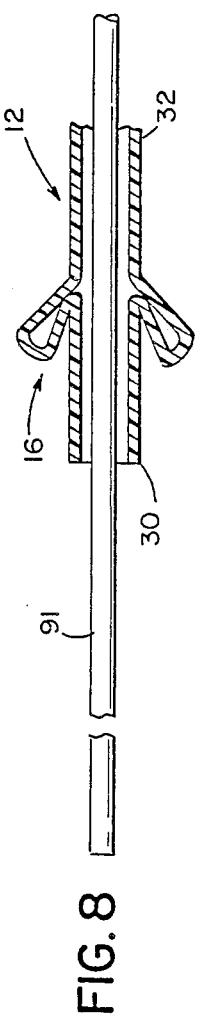
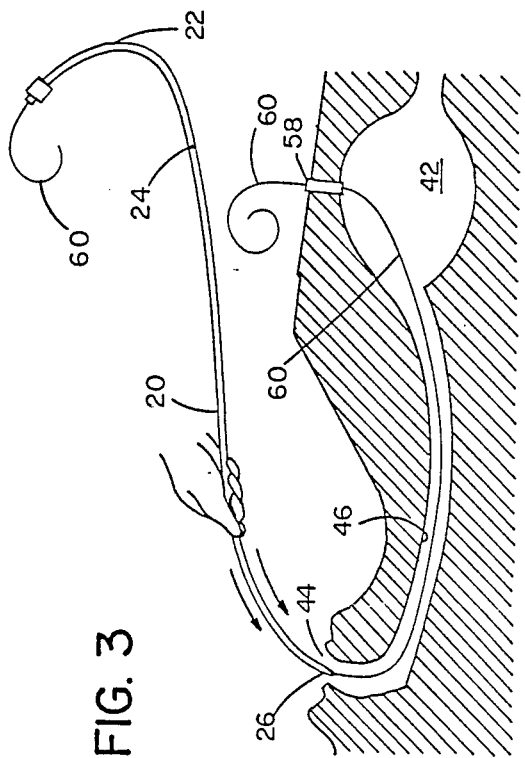
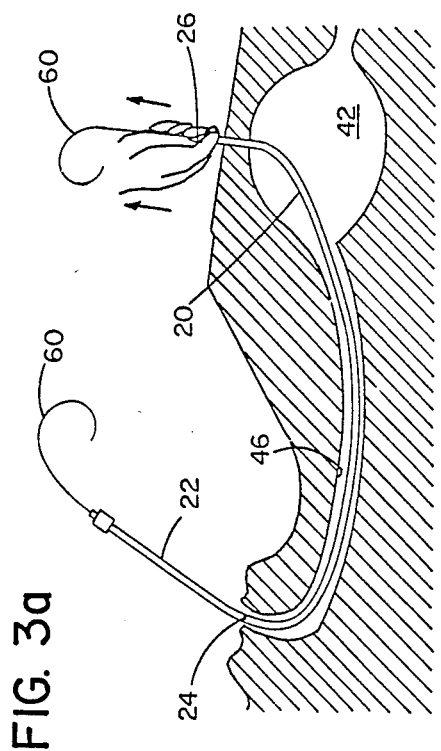
FIG. 1
FIG. 1a
FIG. 8
FIG. 3
FIG. 3a

ENTERAL FEEDING DEVICE

This application is a continuation, of application Ser. No. 054,572, filed May 27, 1987, now abandoned.

The invention relates to enteral feeding catheters which are positioned by surgeons or gastroenterologists in openings through the abdominal wall. Such catheters are used with patients suffering from stroke, Alzheimer's Disease, throat cancer, or other conditions restricting use of the jaws, mouth, throat or esophagus.

One procedure to position the catheter has employed a length of suture thread to pull the catheter from the mouth, down the esophagus into the stomach and out through a puncture opening, see Ponsky and Gauderer. "Percutaneous endoscopic gastrostomy: a nonoperative technique for feeding gastrostomy," Gastrointestinal Endoscopy, Vol. 27, No. 1, 1981, pp. 9–11. In this procedure, a resilient retainer tube sometimes referred to as a "bumper" has been disposed on the catheter between the stomach wall and an enlarged locking formation on the catheter. This bumper tube has openings through its side walls, perpendicular to its axis. The catheter extends through these openings so that the bumper tube lies cross-wise to the catheter, with its round exterior surface bearing against the stomach wall.

Catheters of this type are secured to the patient by a retention disc or similar device that bears upon the exterior of the abdomen about the opening and by a retaining device within the stomach that is sized larger than the opening. Typically the device in the stomach has been of collapsible construction, either a deflatable bulb (Matthews et al. U.S. Pat. No. 3,253,594; Shermeta U.S. Pat. No. 3,915,171; and Moosum U.S. Pat. No. 3,961,632 and U.S. Pat. No. 4,077,412) or a device with wings which can be collapsed to a smaller diameter when a stylet is pushed through the catheter to engage the device (Coanda U.S. Pat. No. 3,241,554 and Nawash et al. U.S. Pat. No. 4,393,873).

Objectives of the invention are to provide an enteral feeding catheter arrangement which improves the positioning procedure used by the surgeon; reduces trauma and risk to the patient; is comfortable to the patient and resists inadvertent displacement; and provides an improved seal about the stomach opening to reduce risk of infection or irritation due to escape of stomach fluids.

SUMMARY OF THE INVENTION

According to one aspect of the the invention, an enteral feeding catheter is characterized by being adapted for introduction through the mouth via a guidewire that extends from the mouth through the esophagus, stomach and abdominal puncture. The catheter has a relatively stiff leading portion of length sufficient to extend along the guidewire from the mouth through the abdominal puncture and of stiffness sufficient to permit it to be pushed from the mouth until it exits at the abdominal puncture and can be grasped. At least an initial length of this leading portion is tapered to a narrow leading tip so that as the tapered part is drawn through the puncture opening, the opening is gradually dilated. The catheter also has a relatively soft, large diameter trailing portion concentrated to the leading portion. This soft portion is adapted to be drawn along the guidewire by grasping and pulling the stiff leading portion, until the leading end of the soft portion extends outside the body through the widened puncture while its trailing end remains in the stomach, thus to provide the conduit for enteral feeding.

In preferred embodiments of this aspect of the invention, the relatively soft training portion of the catheter includes the locking means described below or includes a permanent fixed lock or a fixed bumper which cannot be removed; the length of the leading portion is about 60 cm; and the portion of the catheter adapted to serve as a conduit for enteral feeding has an inner diameter of at least about 3 mm.

According to another aspect of the invention, an enteral feeding device comprises a catheter adapted to introduce sustenance into the body, the portion of the catheter which extends through the abdominal wall and into the stomach being sufficiently soft to avoid irritation of surrounding tissue, the catheter having retractable locking means for use with a retainer within the stomach, immediately distal of the locking means, and the device further including a retainer of a size greater than the puncture in the stomach wall, disposed closely about the catheter between the locking means and the stomach wall, the retainer having an opening of predetermined size, and the retainer being sufficiently soft to avoid irritation of stomach tissue; the locking means comprising a multi-wing formation disposed about the surface of the catheter, each wing comprising a proximal component and a distal component, each component having significant thickness, the inner ends of the components of each wing being joined to the catheter, the outer ends of the components being joined to each other, the locking means being adapted to extend radially beyond the outer diameter of the catheter to inhibit passage of the end of the catheter through the opening in the retainer, the opening having diameter close to the local outer diameter of the catheter, and, in locking position, the proximal and distal components of the wings of the locking means lying at acute angles measured from the axis of the catheter portion within the stomach, and the joined ends of the wing components lying closely adjacent each other, whereby, when force is applied to draw the catheter proximally into the opening, the wing proximal component engages upon the retainer surface defining the opening and thus is urged distally, toward the wing distal component, which is urged toward the surface of the portion of the catheter within the stomach, the wing components thereby providing, in combination, a relatively large, compared to the opening in the retainer, fixed protuberance about the catheter portion, to prevent passage of the catheter through the opening absent application of abnormally high pulling force.

In preferred embodiments of the above described enteral feeding catheters having locking means, the wings are integral with the catheter; the wings are provided by slitting the wall of the catheter longitudinally over a predetermined length, and forming the segment of the wall lying between pairs of the slits into the locking wing; the locking means are adapted to be retracted to permit passage of the catheter through the retainer opening when the catheter portion is urged distally relative to the body of the catheter proximal of the locking means; and creases are formed at the ends of the wing components to provide flexible hinges for resisting return of the wings to an axially aligned configuration during exposure to the heat of sterilization, preferably the wing components and creases form spring means adapted to urge the distal portion of the wing to underlie the proximal portion in locking configuration.

In preferred embodiments where the catheter portion is an open-ended conduit, the locking means are adapted for retraction when the inner surface of the catheter portion is engaged and urged distally relative to the body of the catheter proximal of the locking means.

In preferred embodiments of the enteral feeding device, it further comprises a feeding catheter sized for passage via the catheter into the body; and it comprises an elongated releasing means sized to extend from outside the body through the catheter into the catheter portion, and having an expansible head portion adapted for expansion within the catheter portion to engage the surface of the catheter portion; when the releasing means with the head expanded is urged distally within the catheter, the catheter portion is urged distally to release the locking means.

According to still another aspect of the invention, a method of positioning the enteral feeding device is provided.

Other features and advantages of the invention will be understood from the following description of the presently preferred embodiment, and from the claims.

PREFERRED EMBODIMENT

We first briefly describe the drawings.

DRAWINGS

FIG. 1 is a plan view, partially in section, of the preferred embodiment of the enteral feeding device of the invention with a releasable lock, while FIG. 1a is a similar view of the distal end of the device of the invention with a permanent lock;

FIGS. 2 through 2f are a sequence of diagrammatic views showing generally the procedure for positioning the enteral feeding device, while FIGS. 3 and 3a are diagrammatic views especially showing how the features of device are employed in the positioning procedure;

FIG. 4 is an enlarged section view showing the enteral feeding catheter of FIG. 1 in position, while

FIG. 8 is a side section view showing a modified device for e.g., jejunal feeding.

Figure 2:
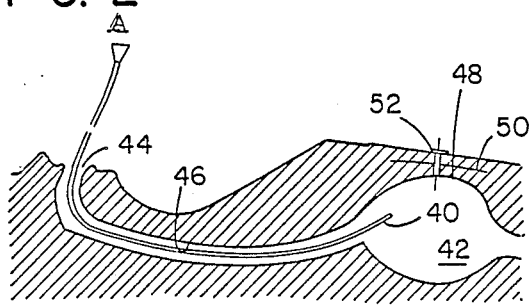

Referring to the figures, the enteral feeding device comprises elongated catheter 12, e.g. about 100 cms long, formed by leading and trailing segments 20 and 22, and a retainer 18 disposed about the catheter immediately preceding a lock means adjacent the trailing end. The lock means may have the form of multi-wing releasable lock 16 (FIG. 1) or a conical permanent lock 17 (FIG. 1a) may be used in situations where it is necessary for the device to resist pull out forces much in excess of those normally experienced, and where it is not necessary to remove the feeding catheter proximally through the opening in the retainer.

Leading and trailing segments 20, 22 are of distinctly different physical characteristics, both selected to enable gas sterilization at temperature of, e.g., 120°–140° F. These segments are joined at 24, e.g. by a press fit utilizing a 2-sided, barb fitting 25. Leading segment 20 has a length of about 60 cm and is formed of material sufficiently rigid to enable the catheter to be pushed without kinking or buckling along a guidewire extending axially through the catheter. A preferred material is polyethylene, with a wall thickness of about 0.037 inch (0.94 mm). The leading segment 20 is tapered over a length of 14 cm from an outer diameter of about 14 French (0.0190 inch or 4.83 mm) to a relatively small tip 26 of about 5 French (0.065 inch or 1.65 mm). At the leading end, the wall thickness is about 0.010 inch (0.25 mm), with an I.D. of about 0.045 inch (1.14 mm), to allow easy passage of an 0.038 inch guidewire.

The trailing segment 22 of catheter 12 has a length of about 45 cm and is of a much different material, selected for biocompatibility and inertness to stomach fluids, and for softness, e.g., optimally approaching the softness of body tissue, to avoid irritation of tissue within the stomach during the time the device is in place, which may be for ten days up to one year. The outer diameter of the trailing segment is about 0.184 inch (4.67 mm) and the inner diameter is about 0.130 inch (3.3 mm). The softness of the material selected is also a trade-off of avoiding irritation while providing strength and springiness for operation of the releasable lock, especially when the lock is formed of the tube material as described below. In this case a durometer of about 80 A is preferred. Materials that have the desired softness and other necessary characteristics include urethane, silicone, and materials solid under the trademarks "C-Flex ®" (sold by Concept Inc., of Clearwater, Fla.), and PERCU-FLEX ® (provided by Medi-Tech, Inc., of Watertown, Mass.). The outer diameter of the trailing segment is constant at about 14 French over its length to the open training end 28. (It is desired to provide a large bore diameter for passage of highly viscous sustenance into the stomach.)

The multi-wing releasable lock 16 adjacent the trailing end is formed from the wall of the catheter by slitting the catheter longitudinally over a predetermined length, 10.5 mm, at a selected number of points about the catheter circumference, as shown, four slits at 90 degrees provide four wings about 3.5 mm wide. The trailing portion 30 of the catheter that will extend into the stomach is moved axially in the direction of the main catheter body 32 to bow the wings radially outwardly and the wings are heat formed into the desired configuration, as described below.

The conical fixed lock 17 has an annular protuberance shape formed from a biocompatible material and of size and dimension to be relatively rigid as compared to the catheter or the retainer. The protuberance is affixed, e.g., by insert molding, about the feeding catheter 32 adjacent the distal end 28. The outer diameter, $D_A$, of the lock is much greater than the diameter, $D_O$, of the opening in the retainer 18 to prevent removal therethrough. The method of forming the fixed lock about the catheter is also described below.

The retainer tube 18 is also formed of a biocompatible material and is soft, e.g. in the preferred embodiment, retainer 18 is C-FLEX ® tubing of 0.375 inch (9.5 mm) outer diameter and 0.250 inch (6.3 mm) inner diameter, having durometer of about 50 A, cut to length of about 1 inch (2.54 cm), with a pair of aligned holes approximately midlength, perpendicular to the retainer axis, of 0.104 inch (2.64 mm) diameter, smaller than the local diameter of the catheter. Thus the retainer tube fits snugly about the catheter. Due to its softness and its snug fit, the retainer tube provides a seal about the catheter to prevent leakage of stomach fluids into the abdominal cavity which would cause infection or irritation.

Figure 2C:
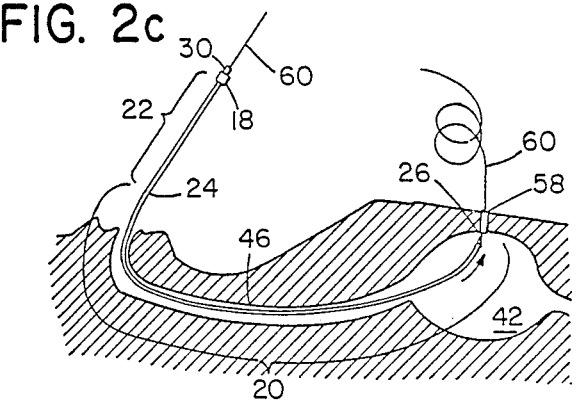
Figure 2A:
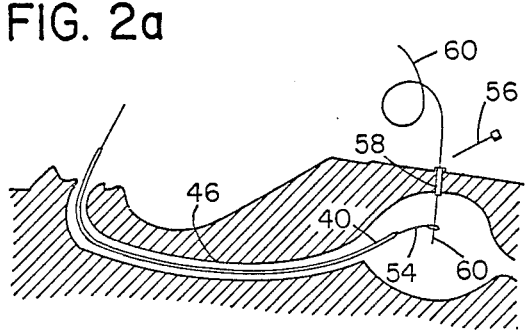
Figure 2D:
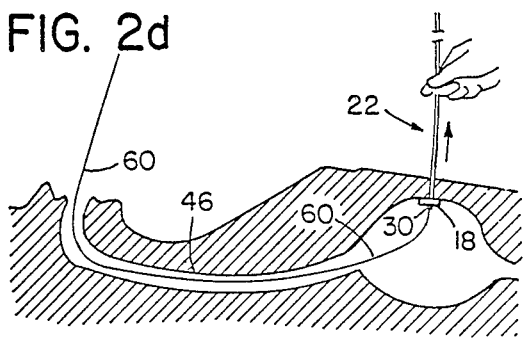
Figure 2B:
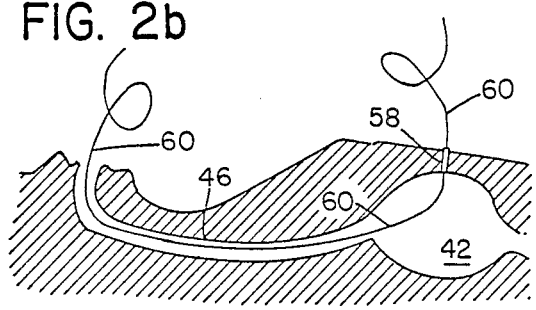
Figure 2E:
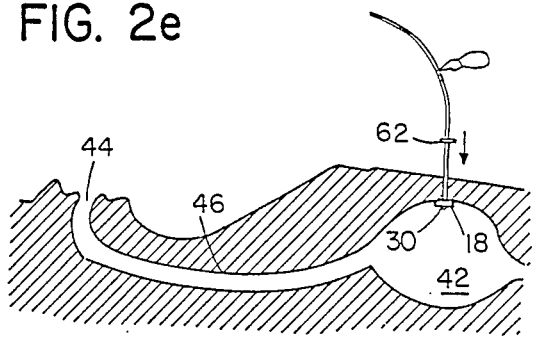
Figure 2F:
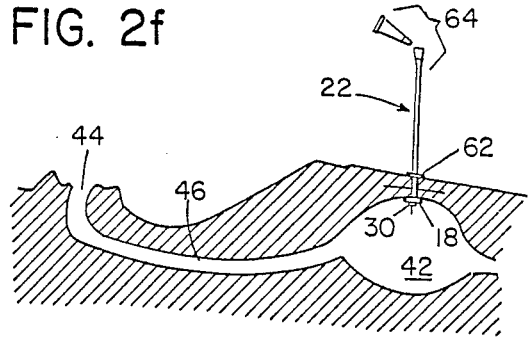

Referring to FIGS. 2 through 2f, and to FIGS. 3 and 3a, the procedure for positioning the enteral feeding device will be described.

A gastroscope 40 is introduced into the stomach 42 via the patient's mouth 44 and esophagus 46. The stomach is inflated with air to distend the stomach wall 48 into contact with the abdominal wall 50. A puncture site is selected, visualized externally from the glow of the gastroscope light shining internally against the stomach wall.

With the tissue suitably anesthetized, a short incision (1.0 to 1.5 cm) is made in the skin and the soft tissues spread with a hemostat.

A Seldinger 18 gauge guide wire introduction needle 52 is introduced in a rapid motion at the site of the small incision, through the abdominal wall, peritoneum, and into the stomach. The needle can easily be seen through the gastroscope as it enters the stomach (FIG. 2).

At this stage a snare 54 is introduced by the gastroscope and positioned just below the needle point, open to its maximum extent.

The Seldinger stylet 56 is removed, leaving the Seldinger cannula 58. A 300 cm, 0.038 inch (0.97 mm) diameter guidewire 60 is introduced through the needle within the stomach where it is entrapped in the snare (FIG. 2a).

The gastroscope and its snare are withdrawn through the esophagus, drawing the wire with it. At the same time, the guidewire is advanced from the exterior through the needle so that no tension is present. When the snare emerges from the mouth with the leading end of the guidewire, the wire can be pulled gently until an adequate amount projects from the mouth (FIG. 2b) while a length still projects from the abdominal side.

A liberal amount of lubricant is placed on the guidewire at the mouth and around the catheter. This end of the guidewire is inserted into the tapered leading tip 26 of the relatively stiff segment 20 of the catheter, and the catheter is pushed over the guidewire and advanced into the mouth.

Referring now also to FIGS. 3 and 3a, the catheter is steadily advanced by pushing on relatively stiff leading portion 20 at the mouth until resistance is felt, usually as the tip 26 reaches the needle. At that stage, with slight tension being placed on the guidewire at both ends to keep it firm, slightly more pressure is applied to the trailing end of the leading portion of the catheter at the mouth until its narrow tip 26 passes through the enteral stomach wall and the enteral abdominal wall and exits at the skin surface (FIG. 2c).

As mentioned above, the length of the stiff leading portion 20 of the catheter is pre-selected so that the trailing end still protrudes from the mouth when the tip exits at the skin surface, to enable the catheter to be advanced by pushing from the mouth until leading tip 26 protrudes from the puncture and can be grasped and pulled. This enables the trailing segment 22, which is to remain in the body, to be of softer, less irritating material, because it is subject to much less force during the placement procedure.

After tip 26 emerges from the abdomen, continual pulling traction is applied to the tip of the relatively rigid leading portion (FIG. 3a) to draw the tapered segment 20 through the puncture opening to dilate the opening gradually, to prepare it for passage of the larger diameter trailing portion. The relatively rigid nature of the tapered segment of the catheter facilitates this procedure. Traction is continued to pull the end of the trailing catheter segment 22 with its retainer and lock down the esophagus, into the stomach to the point where the retainer reaches the puncture opening and is pulled sufficiently against the enteral stomach wall to press it against the peritoneum (FIG. 2d). Optimal position can be confirmed by reintroduction of the gastroscope or by X-ray.

A superficial skin disc 62 is then advanced (FIG. 2e) over the end of the catheter outside the body and secured as by sewing to the skin to hold the device in place, see FIGS. 2f and 3.

After the external catheter is cut to the length desired, a plug 64 is inserted (FIG. 2f) and the device is thus ready for syringe, pump or catheter tube feeding.

Figure 4:
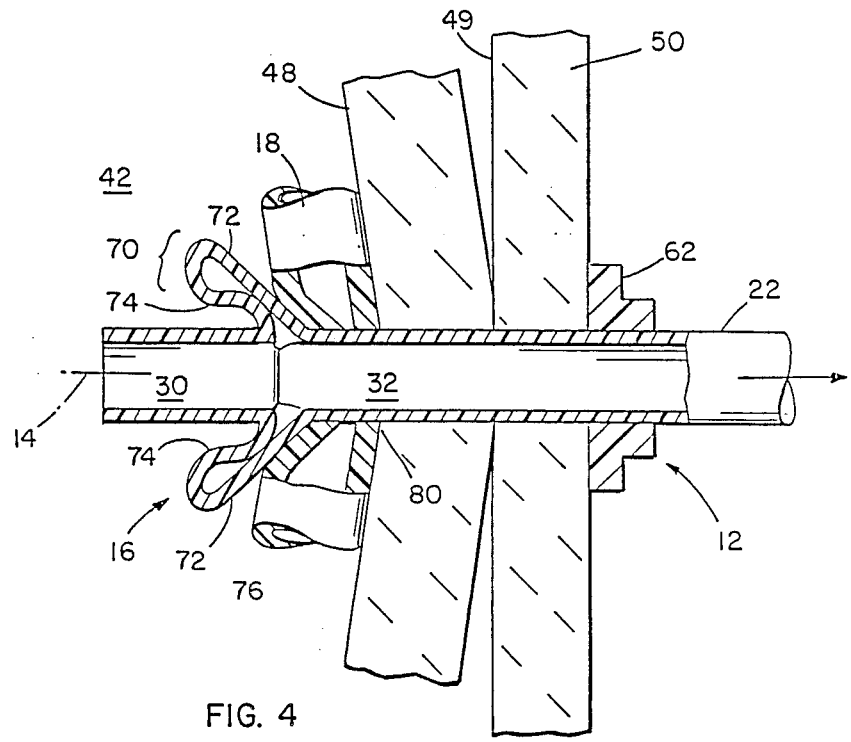
Figure 5:
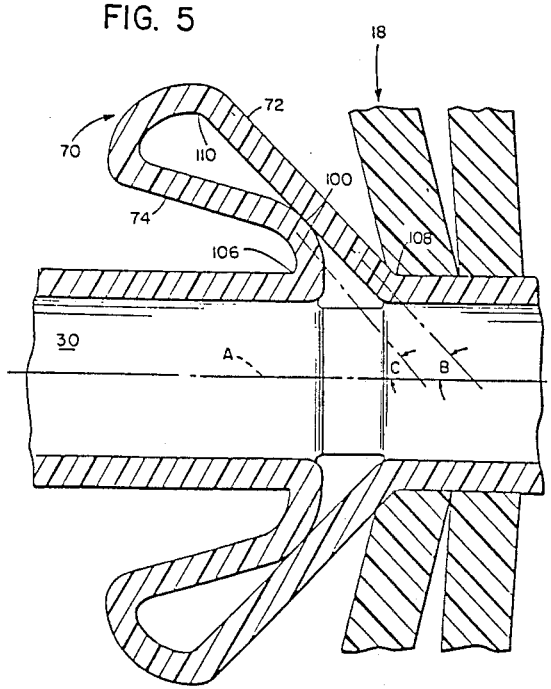
FIGS. 5 and 5a are similar views of the releasable locking means of the device in FIG. 1, showing the device under normal installed tension and under abnormal pulling force, respectively.
Figure 5A:
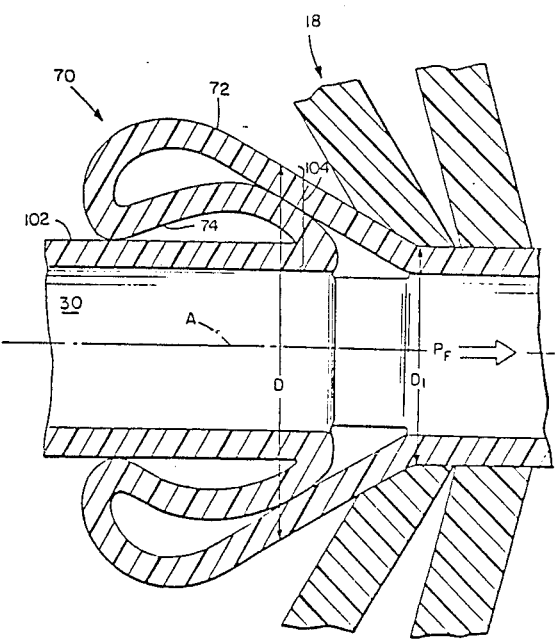

Referring to FIGS. 4, 5 and 5a, important features of the internal locking arrangement of the releasable lock will now be described. The stomach wall 48 is drawn and held against the peritoneum 49 of the abdominal wall 50 by cooperative action of the external retention disc 62 and the internal retainer 18 held in place by multi-wing lock 16. According to a preferred aspect of the invention, lock 16 is formed integrally from the wall of the soft proximal segment 22 of the catheter 12. The special configuration of the lock to be described, even when formed of such soft material, enables resistance to pulling force, e.g. the lock resists forces up to about 11 to 15 lbs.

Each wing 70 of lock 16 (two of four can be seen in FIG. 3) is formed of a proximal wing component 72 and a distal wing component 74, each joined to the catheer at its radial inner end, and the two joined together at their outer radius ends. In normal locking position (FIG. 4), both wing components 72, 74, are angled in the same direction, away from the stomach wall, forming acute angles, B and C, of about 45° to the central axis, A, of the catheter, measured close to the feed tube. Under normal installation tension, pulled against retainer 18, the inner ends of these wing components 72, 74 are at least closely adjacent to each other and preferably engage each other at 100. When abnormal external pulling force is applied, indicated by arrow $P_f$, in FIG. 5, as by accidental movements of the patient, the proximal wing component 72 engages more firmly on surface 76 of the retainer 18 and tends to bend down toward catheter axis A against the distal wing component 74 and the surface 102 of the distal annular tip 30 of the catheter. This tip has sufficient wall thickness to resist collapse under this pulling force. Thus the combined thickness of the two wing components provides an enlarged solid protuberance 104 about the catheter, with an outer diameter, D, significantly larger than the diameter $D_1$ of retainer opening 80, providing substantial resistance to pulling of the catheter through the retainer.

In the preferred form of the lock shown, during molding a sharply angled crease 106 is formed at the inner end of each distal wing component 74, with a corresponding crease of lesser angle at the inner end 108 of each proximal component 76 to cause the distal component to underlie the proximal component.

The point of connection between the outer ends of the wing components is also creased at 110 to reduce elastic memory and form a very flexible hinge which lessens the possibility of the wings assuming their original, axially aligned configuration, e.g., if the lock is opened and closed repeatedly, or from the heat of sterilization.

Figure 6:
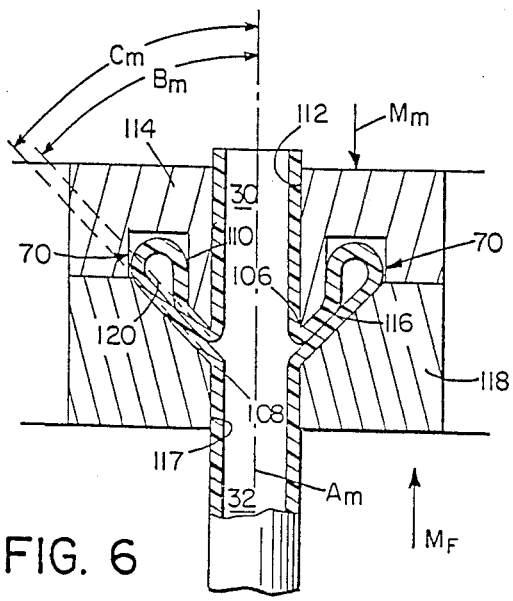
FIG. 6 is a side section view showing the releasable lock means forming process.

The construction of the releasable lock is provided by forming the wings in a heated mold. Referring to FIG. 6, after the catheter is slit, the tip portion 30 is inserted into the bore 112 of a male mold element 114 having a conical surface 116 lying at an angle $B_m$, about 45°, to the mold axis $A_m$, aligned with the axis of the catheter tip. The wings 70 are folded against the surface of the mold, and the bore 117 of a correspondingly shaped female mold element 118 having surface 120 lying at an angle $C_m$, also about 45°, to the mold axis is passed over the body 32 of the catheter. The opposed surfaces of the mold are urged together, arrows $M_M$, $M_F$, while heat is applied at temperature above the temperature of sterilization but below the melting point of the plastic. Referring also to FIG. 5, the pressure and heat of molding cause the sharp crease 106 at the base of the distal wing component 74 with significant thinning compared to the catheter tip and wing component adjacent the crease at both sides. Creases are also formed at 108, at the base of the proximal wing component 72, and at 110, where the wing components join at the tip.

Upon cooling, the components remain at the angles imparted by molding.

Figure 6A:
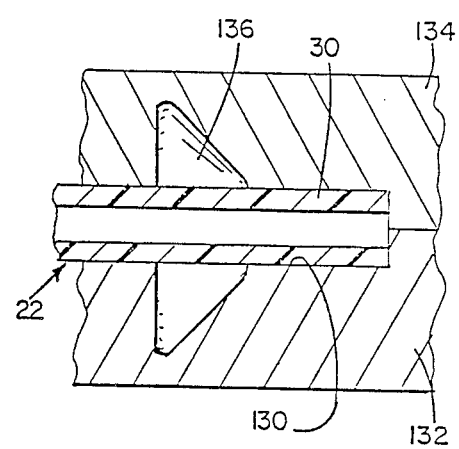
FIG. 6a is a similar view showing the permanent lock means forming process.

Referring to FIG. 6a, the construction of the fixed lock is provided by inserting the tip 30 of the trailing portion 22 of the device into the bore 130 formed by a pair of opposed mold elements 132, 134 which also define annular molding cavity 136 about the body of the catheter. The mold is closed and the material of the locking protuberance is injected into cavity and allowed to cure about the body to form the lock.

After ten days to two weeks, the stomach is usually well attached to the enteral peritoneum and the catheter can be changed should it become clogged, or when the patient recovers, the catheter will need to be removed.

Figure 7:
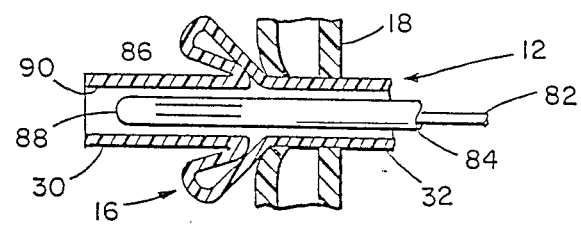
FIGS. 7 through 7b are a sequence of diagrammatic views showing removal of the enteral feeding device of FIG. 1.
Figure 7A:
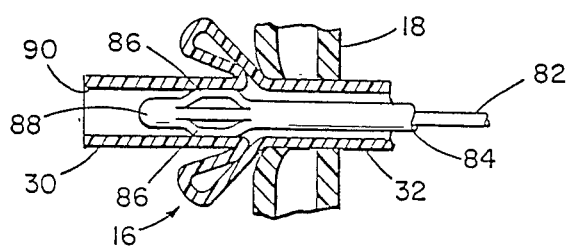
Figure 7B:
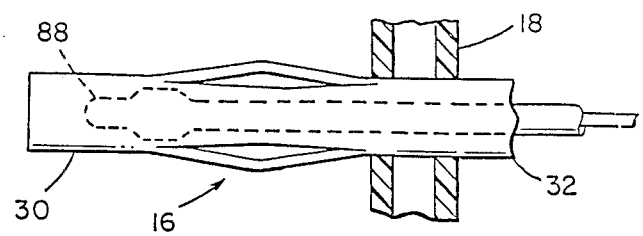

To release the releasable lock within the stomach lumen, the tip 30 of the catheter 12 is urged distally relative to the body 32 of the catheter to a point where the distal wing components 74 no longer underlie the proximal wing components 76. Referring to FIGS. 7 through 7b, a special appliance for releasing the lock of an open-ended catheter is shown. A stylet 82 is inserted into the bore of a closed-tip releasing device 84 having elastically expansible wings 86 adjacent its head 88. The stylet is pushed against the head to retract the wings, and is held while the device is inserted along the bore of the catheter 12 until the wings 86 are within the catheter tip 30. The stylet is withdrawn to allow the wings 86 to expand with force to engage and grip the inner wall 90 of the catheter tip 30 (FIG. 6a). The device 84 is urged distally to move the catheter tip 30 relative to the catheter body 32, thus stretching out the distal and proximal ends to lie end to end at a smaller diameter, thus to release the lock 16. The catheter and lock will then slide through the retainer and out of the body. The retainer 18 remains to be passed spontaneously through the bowel, or it can be retrieved by use of a gastroscope.

Where the device has a fixed lock, it can also be retrieved by use of a gastroscope, or passed spontaneously through the bowel.

Other Embodiments

Other embodiments are within the following claims. For example, at the intersection 24, the trailing segment of the catheter may have an outer diameter significantly less than the outer diameter of the leading segment. Also, the catheter may have a tip of other configuration, e.g., a closed tip with side openings. In such cases, the lock 16 may be released with a stylet inserted through the catheter and pressed against the closed end. The wings of the lock may be formed of other material and joined to the catheter body, as may the distal catheter portion, especially where it forms a short tip extending into the stomach. The catheter portion distal of the locking means may also be of extended length, to form a conduit into the stomach, or beyond.

Referring to FIG. 8, where desired, a smaller diameter enteral feeding device 91 can be advanced over a guidewire through the lumen of the in-dwelling catheter 12 of the invention. This can be passed beyond the pylorus, the duodenum and even past the ligament of Treitz for jejunal feeding.

Where the fixed lock is employed, the retainer may be permanently affixed to the outer wall of the catheter, e.g. by use of adhesive 140 (FIG. 1a); or the retainer so affixed may be used without the annular protuberance of the fixed lock.

What is claimed is:

1. A enteral feeding device comprising
    a catheter adapted to serve as a conduit for passage of sustenence through an abdominal wall into the body, the portion of said catheter which extends through said abdominal wall and into the stomach being sufficiently soft to avoid irritation of stomach tissue,
    said catheter having retractable locking means for use with a retainer within the stomach, immediately distal of said locking means, and
    said device further comprising a retainer of a size greater than the puncture in the stomach wall, disposed closely about said catheter between said locking means and said stomach wall,
    said retainer having an opening of predetermined size, and
    said retainer being sufficiently soft to avoid irritation of stomach tissue;
    said locking means comprising a multi-wing formation disposed about the surface of said catheter, each said wing comprising a proximal component and a distal component, each said component having significant thickness, the inner ends of the components of each wing being joined to said catheter, the outer ends of said components being joined to each other,
    said locking means being adapted to extend radially beyond the outer diameter of said catheter to inhibit passage of the end of the catheter through said opening in said retainer, said opening having diameter close to the local outer diameter of said catheter, and,
    in locking position, the proximal and distal components of the wings of said locking means lying at acute angles measured from the axis of said catheter portion within the stomach, and the joined ends of said wing components lying closely adjacent each other,
    wherey, when force is applied to draw said catheter proximally into said opening, the proximal wing component engages upon the retainer surface defining said opening and thus is urged distally, toward the distal wing component, which is urged toward the surface of the portion of said catheter within the stomach, said wing components thereby providing, in combination, a relatively large, compared to said opening in said retainer, fixed protuberance about said catheter portion, to prevent passage of said catheter through said opening absent application of abnormally high pulling force.

2. The enteral feeding catheter of claim 1 wherein the portion of said catheter adapted to serve as a conduit for enteric feeding has an inner diameter of at least about 3 mm.

3. The enteral feeding catheter of claim 1 wherein said wings are integral with said catheter.

4. The enteral feeding catheter of claim 3 wherein said wings are provided by slitting the wall of said catheter longitudinally over a predetermined length, and forming the segment of said wall lying between pairs of said slits into a said locking wing.

5. The enteral feeding device of claim 1 wherein said locking means are adapted to be retracted to permit passage of said catheter through said retainer opening when said catheter portion is urged directly relative to the body of said catheter proximal of said locking means.

6. The enteral feeding catheter of claim 5 wherein said catheter portion is an open-ended conduit, and said locking means are adapted for retraction when the inner surface of said catheter portion is engaged and urged distally relative to the body of said catheter proximal of said locking means.

7. The enteral feeding device of claim 6 wherein said device further comprises a feeding catheter sized for passage via said catheter into the body.

8. The enteral feeding device of claim 6 further comprising an elongated releasing means sized to extend from outside the body through said catheter into said catheter portion, and having an expansible head portion adapted for expansion within said catheter portion to engage the surfaces of the catheter portion and, when said releasing means with said head expanded is urged distally within said catheter, to urge said catheter portion distally to release said locking means.

9. The enteral feeding device of claim 1 wherein creases are formed at the ends of said wing components to provide flexible hinges for resisting return of said wings to an axially aligned configuration during exposure to the heat of sterilization.

10. The enteral feeding device of claim 9 wherein said wing components and creases form spring means adapted to urge the distal portion of the wing to underlie the proximal portion in locking configuration.

11. A method for introducing an enteral feeding catheter through the mouth via a guidewire that extends from the mouth through the esophagus, stomach and abdominal puncture, said catheter comprising a relatively stiff leading portion of length sufficient to extend along said guidewire from the mouth through said abdominal puncture and said catheter comprising a relatively sift, large diameter trailing portion connected to said leading portion, said method comprising pushing said catheter along said guidewire from the mouth until the leading portion of said catheter exits at said admonial puncture and can be grasped, and thereafter drawing said catheter along said guidewire by grasping the portion of said catheter that has exited said abdominal puncture and pulling until the leading end of said soft portion extends outside the body through said puncture while its trailing end remains in the stomach, whereby the relatively soft trailing portion of said catheter can serve as a conduit for enteral feeding.

12. The method of claim 11 wherein at least an initial length of said leading portion of said catheter is tapered to a narrow leading tip, and said method further comprises gradually dilating said puncture opening as said tapered part is drawn therethrough.

13. A gastrostomy set for placing an enteral feeding catheter in an abdominal puncture to enable feeding directly to the stomach, said set comprising a guidewire of a length sufficient to extend from the outside, through the abdominal puncture, the stomach, the esophagus and out of the mouth, and an elongated catheter member comprising leading and trailing portions, said catheter member being open at both ends to enable passage thereof over the guidewire, and said leading portion being of a length sufficient to extend along said guidewire from outside, through the mouth, the esophagus and stomach and through said abdominal puncture to the outside, said leading portion being tapered to a relatively small opening to accommodate said guidewire and being of stiffness sufficient to permit it to be advanced along said guidewire solely by pushing forces applied at said mouth until the leading end of said portion emerges on said guidewire from said abdominal puncture and may be grasped, said trailing portion of said catheter member being softer relative to said leading portion, adapted to form the feeding tube that is to remain in the patient, said trailing portion being adapted to be drawn along said guidewire which passes therethrough, which guidewire extends from outside the mouth through the esophagus, the stomach, and out through the abdominal puncture in a relatively fixed condition, by grasping and pulling said emerged leading portion of said catheter member, until only the trailing end of said trailing portion remains in the stomach, to serve as a conduit for enteral feeding, the entire movement of said catheter member from the mouth, through the esophagus, the stomach and out through the abdominal puncture being controlled by said relatively fixed guidewire.

14. A catheter member for forming an enteral feeding catheter in an abdominal puncture to enable feeding directly to the stomach, said catheter member comprising leading and trailing portions, said catheter adapted for use with a guidewire of a length sufficient to extend from the outside, through the abdominal puncture, the stomach, the esophagus and out of the mouth, said catheter member being open at both ends to enable passage thereof over the guidewire which is in a relatively fixed condition, and said leading portion of said catheter member being of a length sufficient to extend along said guidewire from outside, through the mouth, the esophagus and stomach and through said abdominal puncture to the outside, said leading portion being tapered to a relatively small opening to accommodate said guidwire and being of stiffness sufficient to permit it to be advanced along said guidewire solely by pushing forces applied at said mouth until the leading end of said leading portion emerges on said guidewire from said abdominal puncture and may be grasped, said trailing portion of said catheter member being softer relative to said leading portion, adapted to form the feeding tube that is to remain in the patient, said trailing portion being adapted to be drawn along said relatively fixed guidewire which passes therethrough, the opposite ends of which guidewire extend out of the mouth and out of the abdominal puncture, respectively, by grasping and pulling said emerged end of said leading end of the leading portion of said catheter member, until only the trailing end of said trailing portion remains in the stomach, to serve as a conduit for enteral feeding, the entire movement of said catheter member from the mouth, through the esophagus, the stomach, and out through the abdominal puncture being controlled by said relatively fixed guidewire.

15. The enteral feeding catheter of claim 13 or 14 wherein the length of said leading portion is about 60 cm.

16. The enteral feeding device of claim 13 or 14 further comprising a bumper means disposed about the trailing end of the soft trailing portion of the cathetrer within the stomach, the trailing end of said catheter, distal of said bumper, having the form of a permanently fixed lock over which the bumper means cannot pass.

17. The enteral feeding device of claim 13 or 14 further comprising a fixed bumper means permanently disposed about the trailing end of the soft trailing portion of the catheter within the stomach.

18. The enteral feeding catheter of claim 13 or 14 wherein the portion of said catheter adapted to serve as a conduit for enteric feeding has an inner diameter of at least about 3 mm.

19. A catheter member for forming an enteral feeding catheter in an abdominal puncture to enable feeding directly to the stomach, said catheter member comprising leading and trailing portions, sid catheter adapted for use with a guidewire of a length sufficient to extend from the outside, through the abdominal puncture, the stomach, the esophagus and out of the mouth, said catheter member being open at both ends to enable passage thereof over the guidewire, and said leading portion of said catheter member being of a length sufficient to extend along said guidewire from outside, through the mouth, the esophagus and stomach and through said abdominal puncture to the outside, said portion being shaped and being of stiffness sufficient to permit it to be advanced along said guidewire solely by pushing forces applied at said mouth until the leading end of said portion emerges on said guidewire from said abdominal puncture to be grasped, said trailing portion of said catheter member being softer relative to said leading portion, adapted to form the feeding tube that is to remain in the patient, said trailing portion being adapted to be drawn along said guidewire by grasping and pulling the leading portion of said catheter member, until only the trailing end of said trailing portion remains in the stomach, to serve as a conduit for enteral feeding, said catheter having retractable locking means associated with its trailing portion adapted for use with a retainer having an opening of predetermined size, and said catheter having a portion within the stomach, immediately distal of said locking means;

said locking means comprising a multi-wing formation disposed about the surface of said catheter, each said wing comprising a proximal component and a distal component, each said component having significant thickness, the respective inner end of each of the proximal and distal components of each wing being joined to said catheter, the respective outer ends of each adjacent pair of proximal and distal components being joined, said locking means being adapted to extend radially beyond the outer diameter of said catheter to inhibit passage of the end of the catheter through said opening in said retainer, said opening having a diameter close to the local outer diameter of said catheter, and, in locking position, the proximal and distal components of the wings of said locking means lying at acute angles measured from the axis of said catheter portion within the stomach, and the joined ends of said wing components lying closely adjacent each other, whereby, when force is applied to draw said catheter proximally into said opening, the proximal wing component engages upon the surface defining said opening and thus is urged distally, toward the distal wing component, which is urged toward the surface of the portion of said catheter in the stomach, said wing components thereby providing, in combination, a relatively large, compared to said opening in said retainer, fixed protuberance about said catheter portion, to prevent passage of said catheter through said opening absent application of abnormally high pulling force.

20. The enteral feeding catheter of claim 19 wherein said locking means are adapted to be retracted to permit passage of said catheter through said retainer opening when said catheter portion is urged distally relative to the body of said catheter proximal of said locking means.

21. The enteral feeding catheter of claim 20 wherein said catheter portion is an open-ended conduit, and said locking means are adapted for retraction when the inner surface of said catheter portion is engaged and urged distally relative to the body of said catheter proximal of said locking means.

22. The enteral feeding catheter of claim 19 wherein said wings are integral with said catheter.

23. The enteral feeding catheter of claim 22 wherein said wings are provided by slitting the wall of said catheter longitudinally over a predetermined length, and forming the segment of said wall lying between pairs of said slits into a said locking wing.

24. The enteral feeding device of claim 19 wherein said locking means are adapted to be retracted to permit passage of said catheter through said retainer opening when said catheter portion is urged distally relative to the body of said catheter proximal of said locking means.

25. The enteral feeding catheter of claim 24 wherein said catheter portion is an open-ended conduit, and said locking means are adapted for retraction when the inner surface of said catheter portion is engaged and urged distally relative to the body of said catheter proximal of said locking means.

26. The enteral feeding device of claim 25 wherein said device further comprises a feeding catheter sized for passage via said catheter into the body.

27. The enteral feeding device of claim 25 further comprising an elongated releasing means sized to extend from outside the body through said catheter into said catheter portion, and having an expansible head portion adapted for expansion within said catheter portion to engage the surfaces of the catheter portion and, when said releasing means with said head expanded is urged distally within said catheter, to urge said catheter portion distally to release said locking means.

28. The enteral feeding device of claim 19 wherein creases are formed at the ends of said wing components to provide flexible hinges for resisting return of said wings to an axially aligned configuration during exposure to the heat of sterilization.

29. The enteral feeding device of claim 28 wherein said wing components and creases form spring means adapted to urge the distal portion of the wing to underlie the proximal portion in locking configuration.

* * * * *